United States Patent
Subramaniyam

(10) Patent No.: US 10,450,246 B2
(45) Date of Patent: Oct. 22, 2019

(54) COMPOSITIONS FOR CONTROL AND INHIBITION OF POLYMERIZATION OF VINYL AROMATIC MONOMERS, AND METHODS OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 15/774,466

(22) PCT Filed: Feb. 9, 2017

(86) PCT No.: PCT/IB2017/050718
§ 371 (c)(1),
(2) Date: May 8, 2018

(87) PCT Pub. No.: WO2017/137924
PCT Pub. Date: Aug. 17, 2017

(65) Prior Publication Data
US 2019/0248718 A1 Aug. 15, 2019

(30) Foreign Application Priority Data
Feb. 13, 2016 (IN) .............................. 201621005100

(51) Int. Cl.
*C09K 3/00* (2006.01)
*C07C 7/20* (2006.01)
(52) U.S. Cl.
CPC ...................................... *C07C 7/20* (2013.01)
(58) Field of Classification Search
CPC ................................... C07C 7/20; C09K 3/00
USPC ............. 252/182.29; 585/435, 436, 440, 441
See application file for complete search history.

(56) References Cited

U.S. PATENT DOCUMENTS

2004/0034247 A1 2/2004 Eldin
2011/0297878 A1 12/2011 Rai et al.

FOREIGN PATENT DOCUMENTS

| IN | 201621005100 | | 2/2016 |
|----|--------------|----|--------|
| WO | 2013102930 | A1 | 7/2013 |
| WO | 2014030131 | A1 | 2/2014 |
| WO | 2017137924 | A1 | 8/2017 |

OTHER PUBLICATIONS

Foreign communication from the priority International Application No. PCT/IB2017/050718, International Search Report and Written Opinion, dated May 16, 2017, 11 pages.
Foreign communication from the priority International Application No. PCT/IB2017/050718, International Preliminary Report on Patentability of the International Preliminary Examining Authority, dated Dec. 7, 2017, 12 pages.

*Primary Examiner* — Thuan D Dang
(74) *Attorney, Agent, or Firm* — Conley Rose, P.C.; Rodney B. Carroll

(57) ABSTRACT

The present invention relates to an improved amine based additive composition for control and inhibition of polymerization of aromatic vinyl monomers, particularly of styrene comprising one or more quinone methide compounds, one or more phenolic compounds and further comprising at least one aliphatic tertiary amine containing —OH group in the alkyl chain. In one embodiment, the present invention also relates to method of use of presently provided composition. In another embodiment, the present invention also relates to method of controlling and inhibiting polymerization of aromatic vinyl monomers, particularly of styrene by employing presently provided composition. In still another embodiment, the present invention also relates to method of preparation of presently provided composition.

18 Claims, No Drawings

COMPOSITIONS FOR CONTROL AND INHIBITION OF POLYMERIZATION OF VINYL AROMATIC MONOMERS, AND METHODS OF USE THEREOF

CROSS REFERENCE TO RELATED APPLICATIONS

This application is a filing under 35 U.S.C. 371 of International Application No. PCT/IB2017/050718 filed Feb. 9, 2017, entitled "Compositions for Control and Inhibition of Polymerization of Vinyl Aromatic Monomers, and Methods of Use Thereof," which claims priority to Indian Patent Application No. 201621005100 filed Feb. 13, 2016, which applications are incorporated by reference herein in their entirety.

FIELD OF THE INVENTION

The present invention relates to compositions for control and inhibition of polymerization of vinyl aromatic monomers, and methods of use thereof, wherein aromatic vinyl monomer includes styrene, wherein improvement comprises a composition of at least one amine with mixture of one or more quinone methide or derivative thereof and one or more phenolic compound.

In one embodiment, the present invention relates to a method of preparation of improved additive composition of present invention for control and inhibition of polymerization of aromatic vinyl monomers including styrene, wherein improvement comprises preparation of composition comprising at least one amine in combination with mixture of one or more quinone methide or derivative thereof and one or more phenolic compound.

In another embodiment, the present invention relates to a method for control and inhibition of polymerization of aromatic vinyl monomers including styrene by employing improved additive composition of present invention, wherein improvement comprises treating the stream containing aromatic vinyl monomers with a composition comprising at least one amine in combination with mixture of one or more quinone methide or derivative thereof and one or more phenolic compound.

BACKGROUND OF THE INVENTION

The polymerization of aromatic vinyl monomers including styrene during processing is a matter of concern, because it causes formation of unwanted polymers and results in loss of yield of end product and makes the process un-economical.

In the art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders alone is that these are not very effective to reduce polymerization of styrene to a level of substantial inhibition or to the acceptable level of inhibition.

The prior art proposes composition comprising a combination of (a) a quinone methide (QM) and (b) 4 hydroxy tempo 2,2,6,6-tetramethyl-,1-oxide (4HT) as styrene polymerization inhibitor. However, the inventor has found [refer to examples and corresponding data] that main problem of using this known composition of QM and 4HT is that even with higher amounts of the composition, the problem of polymerization is not resolved.

The prior art also proposes composition comprising a combination of (a) a quinone methide (QM) and (b) a phenolic compound, for example 2,6-di-tert-butyl phenol (2,6 DTBP) as styrene polymerization inhibitor. However, the inventor has found [refer to examples and corresponding data] that main problem of using this known composition of QM and 2,6 DTBP is that even with higher amounts of the composition, the problem of polymerization is not resolved.

Therefore, the industry is aiming for additive composition wherein the amount of QM and phenolic compound can be reduced or minimized so that the resulted composition is economical as well as safe for human being.

Any effort to reduce or minimize consumption of QM and/or phenolic compound will lessen the problems of the industry.

Need of the Invention

Therefore, there is still a need of an improved additive composition and method of its use and preparation, and method of controlling and inhibiting polymerization of vinyl aromatic monomers including styrene by employing said composition, wherein the additive composition is not only suitable for substantial control and inhibition of polymerization of aromatic vinyl monomers including styrene, but also comprises substantially reduced or minimized amounts of QM and/or phenolic compound.

Therefore, the present invention aims at providing a solution to above-described existing industrial problems by providing an improved additive composition and method of its use and preparation, and method of controlling and inhibiting polymerization of vinyl aromatic monomers including styrene, wherein the additive composition is not only suitable for substantial control and inhibition of polymerization of aromatic vinyl monomers including styrene, but also comprises substantially reduced or minimized amounts of QM and/or phenolic compound.

Objects of the Invention

Accordingly, the main object of present invention is to provide an effective and improved amine based additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises substantially reduced or minimized amounts of QM and/or phenolic compounds. Any effort to reduce or minimize the consumption of QM and/or phenolic compound to any extent will lessen the problems of the industry, and is expected to be preferred by the industry over the known compositions comprising QM and/or phenolic compounds.

Another main object of the present invention is to provide an effective and improved amine based additive composition and method of its use and preparation, and method of controlling and inhibiting polymerization of vinyl aromatic monomers, wherein the additive composition comprises substantially reduced or minimized amount of QM and/or phenolic compound, and is still suitable for substantial control and inhibition of polymerization of aromatic vinyl monomers including styrene, and is still required in relatively lower dosage as compared to dosage of combination of QM and phenolic compounds for achieving the same or better level of control and inhibition of polymerization of styrene.

This is also an object of present invention to provide an effective and improved amine based additive composition and method of its use and preparation, and method of controlling and inhibiting polymerization of vinyl aromatic monomers, wherein the additive composition comprises at least one amine, and reduced or minimized amount of one or more QM and one or more phenolic compounds, and is still suitable for substantial control and inhibition of polymerization of aromatic vinyl monomers including styrene, and is still required in relatively lower dosage as compared to dosage of combination of QM and/or phenolic compounds for achieving the same or better level of control and inhibition of polymerization of styrene, and wherein the amine comprises aliphatic tertiary amine containing —OH group in the alkyl chain.

The present invention particularly aims at providing an effective and improved amine based additive composition and method of its use and preparation, and method of controlling and inhibiting polymerization of vinyl aromatic monomers, wherein the additive composition comprises at least one amine in combination with reduced or minimized amounts of one or more QM and one or more phenolic compounds and is still suitable for substantial control and inhibition of polymerization of aromatic vinyl monomers including styrene, and is still required in relatively lower dosage as compared to dosage of combination of QM and/or phenolic compounds for achieving the same or better level of control and inhibition of polymerization of styrene, and wherein the amine comprises aliphatic tertiary amine containing —OH group in the alkyl chain, and therefore, the composition of the present invention is not only economical, but is also environment friendly.

The present invention particularly aims at improving the performance of additive compositions comprising a combination of QM and phenolic compounds, wherein the present composition comprises a combination of one or more QM and one or more phenolic compounds, and further comprises at least one amine comprising aliphatic tertiary amine containing —OH group in the alkyl chain.

The present invention aims at improving the performance of additive compositions comprising a combination of QM and phenolic compounds at a wider range of duration of treatment, and temperature, wherein the composition comprises a combination of one or more QM and one or more phenolic compounds, and further comprises at least one amine comprising aliphatic tertiary amine containing —OH group in the alkyl chain.

The present invention aims at improving the performance of additive compositions comprising a combination of QM and phenolic compounds at a wider range of temperature and in presence of air, wherein the composition comprises a combination of one or more QM and one or more phenolic compounds, and further comprises at least one amine comprising aliphatic tertiary amine containing —OH group in the alkyl chain.

It is to be noted that as per the present invention, the term 'quinone methide' or 'QM' is intended to include 'derivatives of quinone methide'.

Other objects and advantages of the present invention will become more apparent from the following description when read in conjunction with examples, which are not intended to limit scope of present invention.

DETAILED DESCRIPTION

With aim to overcome the above-described problems of the prior art and to achieve the above-described objects of the present invention, the inventor has found that when at least one aliphatic tertiary amine containing hydroxyl group in the alkyl chain is added to composition comprising a combination of QM and phenolic compounds, then, surprisingly and unexpectedly, not only polymerization controlling and inhibiting efficiency of the composition comprising the combination of QM and phenolic compounds is substantially improved, but polymerization of aromatic vinyl monomers including styrene, surprisingly and unexpectedly, is also controlled and inhibited to an improved level with substantially reduced and minimized dosage of QM and phenolic compounds in a composition comprising at least one aliphatic tertiary amine containing hydroxyl group in the alkyl chain, and one or more QM and one or more phenolic compounds, which makes the present composition economical as well as environment friendly.

With aim to overcome the above-described problems of the prior art and to achieve the above-described objects of the present invention, the inventor has found that when the aliphatic tertiary amine comprising tris(2-hydroxypropyl) amine (TIPA) is added to a composition comprising a combination of QM and phenolic compounds, then, surprisingly and unexpectedly, not only polymerization controlling and inhibiting efficiency of composition comprising a combination of QM and phenolic compounds is substantially improved, but polymerization of aromatic vinyl monomers including styrene, surprisingly and unexpectedly, is also controlled and inhibited to the an improved level with substantially reduced and minimized dosage of the combination of QM and phenolic compounds in the said composition.

With aim to overcome the above-described problems of the prior art and to achieve the above-described objects of the present invention, the inventor has also found that when the aliphatic tertiary amine comprising N,N,N',N' tetrakis (2-hydroxypropyl) ethylenediamine (Quadrol®), 2,2',2'',2'''-(1,2-Ethanediyldinitrilo)tetraethanol (THEED), a mixture thereof is added to a composition comprising a combination of QM and phenolic compounds, then, polymerization controlling and inhibiting efficiency of the prior art composition comprising a combination of QM and phenolic compounds is also improved, and the polymerization of aromatic vinyl monomers including styrene is also controlled and inhibited to an improved level, but surprisingly and unexpectedly, with marginally increased dosage of the composition as compared to the dosage of the composition comprising QM, phenolic compound and TIPA. Therefore, the compositions comprising N,N,N',N' tetrakis (2-hydroxypropyl) ethylenediamine (Quadrol®), 2,2',2'',2'''-(1,2-Ethanediyldinitrilo)tetraethanol (THEED), or a mixture thereof with a combination of QM and phenolic compounds are second preferred embodiment of the present invention.

With aim to overcome the above-described problems of the prior art and to achieve the above-described objects of the present invention, the inventor has also found that when the aliphatic tertiary amine comprising triethanolamine (TEA), monoethanolamine (MEA), diethanolamine (DEA), and/or tris[N-butylamine] (TBA) is added to a composition comprising a combination of QM and phenolic compounds, then, polymerization controlling and inhibiting efficiency of the prior art composition comprising a combination of QM and phenolic compounds is not improved. Therefore, the compositions comprising triethanolamine (TEA), monoethanolamine (MEA), diethanolamine (DEA), and/or tris[N-butylamine] (TBA) with a combination of QM and phenolic compounds are not in accordance with the present invention.

Accordingly, the present invention relates to an improved amine based additive composition for controlling and inhibiting polymerization of aromatic vinyl monomers including styrene comprising:

(A) one or more quinone methide or derivatives thereof (QM), (B) one or more phenolic compounds, and characterized in that the said composition further comprises:

(C) at least one amine comprising aliphatic tertiary amine containing —OH group in the alkyl chain.

In accordance with one of the embodiments of the present invention, the amine of the present invention makes the present composition economical as well as environment friendly.

In accordance with the most preferred embodiment of the present invention, the aliphatic tertiary amine containing hydroxyl group in the alkyl chain comprises tri-isopropanol amine or tris(2-hydroxypropyl)amine (TIPA).

In accordance with one of the embodiments of the present invention, the aliphatic tertiary amine containing hydroxyl group in the alkyl chain may comprise N,N,N',N'-Tetrakis (2-hydroxyethyl) ethylene-diamine (THEED), N,N,N',N'-Tetrakis (2-hydroxypropyl) ethylene-diamine (Quadrol®), or a mixture thereof. However, as described herein above, the compositions comprising N,N,N',N' tetrakis (2-hydroxypropyl) ethylenediamine (Quadrol®), 2,2',2'',2'''-(1,2-Ethanediyldinitrilo)tetraethanol (THEED), or a mixture thereof with a combination of QM and phenolic compounds are the second preferred embodiment of the present invention.

Therefore, in first embodiment, the present invention relates to an improved amine based additive composition for control and inhibition of polymerization of aromatic vinyl monomers including styrene comprising:

(A) one or more quinone methide or derivatives thereof (QM), (B) one or more phenolic compounds, and characterized in that the said composition further comprises:

(C) at least one amine comprising aliphatic tertiary amine containing —OH group in the alkyl chain, wherein said aliphatic tertiary amine comprises tri-isopropanol amine (TIPA).

Therefore, in accordance with another embodiment of the present invention it relates to the additive composition, wherein the aliphatic tertiary amine containing hydroxyl group in the alkyl chain comprises N,N,N',N'-Tetrakis (2-hydroxyethyl) ethylene-diamine (THEED), N,N,N',N'-Tetrakis (2-hydroxypropyl) ethylene-diamine (Quadrol®), or mixture thereof.

Therefore, in second embodiment, the present invention relates to an improved amine based additive composition for control and inhibition of polymerization of aromatic vinyl monomers including styrene comprising:

(A) one or more quinone methide or derivatives thereof (QM), (B) one or more phenolic compounds, and characterized in that the said composition further comprises:

(C) at least one amine comprising aliphatic tertiary amine containing —OH group in the alkyl chain, wherein said aliphatic tertiary amine is selected from the group comprising:

i) tris(2-hydroxypropyl)amine (TIPA);

ii) and may additionally comprise N,N,N',N'-Tetrakis (2-hydroxypropyl) ethylene-diamine (Quadrol®);

iii) N,N,N',N'-Tetrakis (2-hydroxyethyl) ethylene-diamine (THEED); and iv) a mixture thereof.

The inventor has found that when composition of the present invention comprises at least one of the aliphatic tertiary amine of the present invention, the efficiency of QM and phenolic compounds to control and inhibit polymerization of aromatic vinyl monomers including styrene is, surprisingly and unexpectedly, substantially improved to the an improved level that's too at substantially reduced or minimized dosages of QM and phenolic compounds, thereby making the composition of present invention relatively more economical and environment friendly.

In accordance with one of the embodiments of the present invention, the phenolic compound comprises 2,6-di-tert-butyl phenol (2,6 DTBP), butylated hydroxy anisole (BHA), butylated hydroxy toluene (BHT), or a mixture thereof.

In accordance with one of the embodiments of the present invention, the phenolic compound does not comprise hydroquinone (HQ), particularly it does not comprise 1,4-benzene diol or 1,4-dihydroxy benzene, because the inventor has found that when the phenolic compound is HQ and is in combination with the QM, then surprisingly and unexpectedly, the addition of the aliphatic tertiary amine of the present invention does not improve the polymerization controlling and inhibition efficiency with reduced amount of the QM and HQ.

In accordance with one of the embodiments of the present invention, the said quinone methide or derivatives thereof (QM) comprises benzyl quinone methide, preferably 4-benzylidene,2,6-di-tert-butyl cyclohexa-2,5-dienone.

It may be noted that 'said quinone methide or derivatives thereof' herein after may be referred to as QM.

In accordance with one of the embodiments of the present invention, in the mixture of QM and phenolic compound, the QM may be taken in an amount varying from about 0.2 to about 99.8% by wt. and the phenolic compound may be taken in an amount varying from about 99.8 to about 0.2% by wt. of the mixture of the QM and the phenolic compound.

In accordance with one of the embodiments of the present invention, the mixture of the QM and the phenolic compound may comprise the QM and the phenolic compound in a weight ratio varying from about 99.8:0.2 to about 0.2:99.8.

In accordance with one of the embodiments of the present invention, the said aliphatic tertiary amine or mixture thereof is taken an amount varying from about 0.01 to about 70% by wt. of the composition, preferably varying from about 0.1 to about 50% by wt. of the composition, more preferably varying from about 0.5 to about 30% by wt. of the composition, even more preferably varying from about 1 to about 20% by wt. of the composition.

It may be noted that the stream comprising aromatic vinyl monomers including styrene may be referred to as monomer stream or as aromatic vinyl monomers stream.

In accordance with one of the preferred embodiments of the present invention, the composition of present invention may be added to the stream containing aromatic vinyl monomers including styrene in an amount varying from about 0.01 ppm to about 5000 ppm, preferably varying from about 0.1 ppm to about 3000 ppm, more preferably varying from about 1 ppm to about 2000 ppm, even more preferably varying from about 5 ppm to about 2000 ppm by weight of the stream of the monomers including styrene.

Accordingly, in third embodiment, the present invention also relates to method of using the above-described amine based additive composition of the present invention to control and inhibit polymerization of aromatic vinyl monomers including styrene, wherein the method comprises treating the aromatic vinyl monomers including styrene with the said additive composition.

In accordance with one of the embodiments of the present invention, one or more said QM, one or more said phenolic compounds, and said aliphatic tertiary amine may be added to the monomers stream either individually or after mixing with each other.

It may be noted that all the features of the composition of the present invention described herein, a reference to which is drawn in entirety, are deemed to have been included in present method of using said additive composition of the present invention.

Accordingly, in fourth embodiment, the present invention also relates to method for controlling and inhibiting polymerization of aromatic vinyl monomers including styrene, wherein the method comprises adding the said amine based additive composition of the present invention described herein to the stream comprising aromatic vinyl monomers including styrene.

In accordance with one of the preferred embodiments of the present invention, the method for controlling and inhibiting polymerization of aromatic vinyl monomers including styrene by employing said additive composition of the present invention comprises adding an amount varying from about 0.01 ppm to about 5000 ppm, preferably varying from about 0.1 ppm to about 3000 ppm, more preferably varying from about 1 ppm to about 2000 ppm, even more preferably varying from about 5 ppm to about 2000 ppm of the said composition to the aromatic vinyl monomers stream including styrene based on weight of the monomers.

In accordance with one of the embodiments of the present invention, one or more said QM, one or more said phenolic compounds, and said amine may be added to the monomers stream either individually or after mixing with each other.

It may be noted that all the features of the composition of the present invention described herein, a reference to which is drawn in entirety, are deemed to have been included in the present method for controlling and inhibiting polymerization of aromatic vinyl monomers including styrene by employing said additive composition of the present invention.

In accordance with one of the embodiments of the present invention, the composition of the present invention may be mixed with stream containing aromatic vinyl monomers either before the stream enters into processing system or after the stream has entered into processing system, but preferably the composition is added to the stream containing aromatic vinyl monomers before its processing starts so that polymerization of aromatic vinyl monomers is avoided or minimized.

In accordance with one of the embodiments of the present invention, the present composition may be used over a wide range of temperature varying from about 50 degree C. to about 180 degree C., preferably from about 60 degree C. to about 180 degree C.

The composition of the present invention may be prepared in any known manner to prepare the compositions.

Accordingly, in fifth embodiment, the present invention also relates to a method for preparing said amine based additive composition of the present invention described herein for controlling and inhibiting polymerization of aromatic vinyl monomers including styrene, wherein one or more said QM, one or more phenolic compounds may be mixed with said amine either individually or after mixing with each other.

In particular, in fifth embodiment, the present invention relates to a method for preparation of additive composition of the present invention described herein, a reference to which is drawn in entirety, for controlling and inhibition of polymerization of aromatic vinyl monomers including styrene, wherein said method comprises:

step of mixing (A) one or more quinone methide or derivatives thereof (QM), and (B) one or more phenolic compounds, and characterized in that said QM and said phenolic compounds or mixture thereof is further mixed with (C) said aliphatic tertiary amine.

In accordance with one of the embodiments of the present invention, the method for preparation of additive composition of the present invention comprises mixing the said amine with one or more of the QM and one or more of the phenolic compounds either individually or after mixing with each other.

It may also be noted that all the features of the composition of the present invention described herein, a reference to which is drawn in entirety, are deemed to have been included in the present method for preparation of the additive composition of the present invention.

Further advantages and embodiments of the present invention will become more apparent from the following examples.

The present invention is now described with the help of following examples, which are not intended to limit scope of the present invention, but have been incorporated to illustrate mode and best mode of performing the present invention.

EXPERIMENTS

In the present experiments, the prior art additive is a combination of—quinone methide (4 Benzylidene, 2,6 di Tert Butyl Cyclohexa-2,5 dienone) and 2,6 DTBP, or BHA, or BHT, and the present aliphatic tertiary amine is TIPA, Quadrol, or THEED, and the comparative amines are TEA, DEA, MEA or TBA.

Main Experiment:

In the following experiments, weighed amount of distilled styrene (or hydrocarbon stream in gms) and weighed amount of additives (in ppm by weight of styrene or hydrocarbon stream) were taken in a tube reactor equipped with thermometer and nitrogen inlet and outlet. In these experiments, enough $N_2$ flow was maintained to ensure proper agitation. The reactions were carried out at about 120° C. under continuous nitrogen flow for duration as mentioned in following tables. After the selected duration, the reactor was cooled to below about 10° C. by immersing in crushed ice. The contents of the reactor were then poured in a beaker. To this same beaker, approximately for about 1.5-2 g chilled polymerization mixture, about 80 g methanol was used to precipitate the polymer formed in the styrene solution. The precipitate obtained was filtered, dried to remove methanol, and weighed. The weight of the precipitate formed is reported as % polymer formed.

It may be noted that styrene was purified before use to remove the stabilizers.

The Inventor has also found that neither the amine per se, for example TIPA per se, Quadrol per se, THEED per se is a styrene polymerization inhibitor, nor the phenolic compound per se, for example 2,6 DTBP per se, BHA per se, BHT per se is a styrene polymerization inhibitor (re Table VII. The 200 ppm dosage of TIPA per se from Sterling has shown about 17.08% polymerization and TIPA per se from DOW has shown about 16.16% polymerization of the styrene. Similarly, the 200 ppm dosage of Quadrol per se has shown about 14.64% polymerization and THEED per se has shown about 14.34% polymerization of the styrene. Similarly, 200 ppm dosage of the 2,6 DTBP per se has shown about 16.31% polymerization of the styrene, 200 ppm dosage of the BHA per se has shown about 17.14% polymerization of the styrene, and 200 ppm dosage of the BHT per se has shown about 15.68% polymerization of the styrene.

The combination of QM and the phenolic compound, the prior art additive for the present invention, has shown substantial polymerization of styrene. For example, the 100 ppm dosage of combination of QM and 2,6 DTBP when taken in a weight ratio of 90:10 has shown about 7.62% polymerization of the styrene, combination of QM and BHA in same weight ratio has shown about 10.41% polymerization of the styrene, and combination of QM and BHT in same weight ratio has shown about 7.8% polymerization of the styrene. Similarly, the 200 ppm dosage of combination of QM and 2,6 DTBP when taken in a weight ratio of 90:10 has shown about 3.16% polymerization of the styrene, combination of QM and BHA in same weight ratio has shown about 6.96% polymerization of the styrene, and combination of QM and BHT in same weight ratio has shown about 3.68% polymerization of the styrene.

It may be noted that the combinations of QM and 2,6 DTBP, QM and BHA, and QM and BHT are the prior art compositions of the present invention, and the % polymerization of these combinations is the blank for the test results of the compositions of the present invention and the comparative amines.

Therefore, it would not be obvious to combine the aliphatic tertiary amine per se, for example, TIPA, Quadrol or THEED with the combination of QM and the phenolic compound, i.e. 2,6 DTBP, BHA or BHT.

The Inventor has found that when 4 ppm or 20 ppm of TEA, DEA, MEA or TBA is added to 100 ppm dosage of a combination of QM and 2,6 DTBP in a weight ratio of 90:10, the % polymerization of the styrene does not improve (Re Table I).

The Inventor has found that when 4 ppm of Quadrol® is added to 100 ppm dosage of a combination of QM and 2,6 DTBP in a weight ratio of 90:10, the % polymerization of the styrene reduces to about 6.85%, and on addition of about 20 ppm it reduces to about 4.86% (Re Table I).

The Inventor has found that when 4 ppm of THEED is added to 100 ppm dosage of a combination of QM and 2,6 DTBP in a weight ratio of 90:10, the % polymerization of the styrene reduces to about 6.72%, and on addition of about 20 ppm it reduces to about 5.08% (Re Table I).

However, the Inventor has found that when 4 ppm of TIPA is added to 100 ppm dosage of a combination of QM and 2,6 DTBP in a weight ratio of 90:10, the % polymerization of the styrene substantially reduces to about 4.48%, and on addition of about 20 ppm it substantially reduces to about 3.08% (Re Table I).

Therefore, it would not be obvious to combine the TEA, DEA, MEA or TBA instead of the aliphatic tertiary amine with the combination of QM and the phenolic compound, i.e. 2,6 DTBP.

Same technical effects have been seen with the combinations of QM and BHA (Re table—II), and QM and BHT (Re table—III) for 100 ppm dosage.

With above unexpected and surprising findings the inventor has found that when 20 ppm of TIPA, Quadrol or THEED is added to 200 ppm dosage of the combination of QM and 2,6 DTBP, the % polymerization of styrene, respectively, reduces substantially from 3.18% to 0.21%, 0.53% and 0.44%. On the contrary, the change with addition of TEA, MEA and DEA is marginal (Re Table—IV).

Similarly, with above unexpected and surprising findings the inventor has found that when 20 ppm of TIPA, Quadrol or THEED is added to 200 ppm dosage of the combination of QM and BHA, the % polymerization of styrene, respectively, reduces substantially from 6.96% to 0.34%, 1.69% and 1.54%. On the contrary, substantially no change is observed with addition of TEA, DEA and MEA (Re Table—V).

Similarly, with above unexpected and surprising findings the inventor has found that when 20 ppm of TIPA, Quadrol or THEED is added to 200 ppm dosage of the combination of QM and BHT, the % polymerization of styrene, respectively, reduces substantially from 3.68% to 0.32%, 1.38% and 1.42%. On the contrary, substantially no change is observed with addition of TEA, DEA and MEA (Re Table—VI).

The inventor has also found that the prior art additive—a combination of QM and HQ also does not show substantial improvement on addition of the amine of the present invention, i.e. a combination of QM and HQ with TIPA (re Tables VIII-X).

The inventor has also carried out experiments with prior art additive—quinone methide (4 Benzylidene, 2,6 di Tert Butyl Cyclohexa-2,5 dienone) for 600 ppm dosage for various duration of time varying up to 300 mins for comparison purpose.

The experiments with prior art additives a combination of QM and 2,6 DTBP, and a combination of QM and HQ were also carried out for a composition comprising 600 ppm of QM and 85 ppm of phenolic compound for various duration of time varying up to 300 mins for comparison purpose (re Table VIII), and for a comparative combination of QM and HQ with TIPA are also carried for a composition comprising 600 ppm of QM, 85 ppm of phenolic compound and either 18 ppm or 30 ppm of TIPA for various duration of time varying up to 300 mins for comparison purpose (re Table X).

The experiment with the present additive compositions comprising a combination of QM and 2,6 DTBP with TIPA were also carried for a composition comprising 600 ppm of QM, 85 ppm of phenolic compound and either 18 ppm or 30 ppm of TIPA for various duration of time varying up to 300 mins for comparison purpose (re Table IX).

TABLE I (100 ppm dosage) QM/2,6 DTBP/Amine

| Active Dosage, ppm | QM + 2,6DTBP + TIPA | QM + 2,6DTBP + TEA | QM + 2,6DTBP + DEA | QM + 2,6DTBP + QUADROL | QM + 2,6DTBP + THEED | QM + 2,6DTBP + MEA | QM + 2,6DTBP + TBA |
|---|---|---|---|---|---|---|---|
| 90 + 10 + 0 | 7.62 | 7.62 | 7.62 | 7.62 | 7.62 | 7.62 | 7.62 |
| 90 + 10 + 4 | 4.48 | 7.55 | 7.52 | 6.85 | 6.72 | 7.51 | 7.54 |

TABLE I-continued

| | (100 ppm dosage) QM/2,6 DTBP/Amine | | | | | | |
|---|---|---|---|---|---|---|---|
| Active Dosage, ppm | QM + 2,6DTBP + TIPA | QM + 2,6DTBP + TEA | QM + 2,6DTBP + DEA | QM + 2,6DTBP + QUADROL | QM + 2,6DTBP + THEED | QM + 2,6DTBP + MEA | QM + 2,6DTBP + TBA |
| 90 + 10 + 10 | 3.89 | 7.59 | 7.61 | | | 7.59 | 7.58 |
| 90 + 10 + 15 | 3.4 | 7.51 | 7.48 | | | 7.48 | 7.61 |
| 90 + 10 + 20 | 3.08 | 7.48 | 7.53 | 4.86 | 5.08 | 7.54 | 7.52 |

TABLE II

| | (100 ppm dosage) QM/BHA/Amine | | | | | | |
|---|---|---|---|---|---|---|---|
| Active Dosage, ppm | QM + BHA + TIPA | QM + BHA + TEA | QM + BHA + DEA | QM + BHA + QUADROL | QM + BHA + THEED | QM + BHA + MEA | QM + BHA + TBA |
| 90 + 10 + 0 | 10.41 | 10.41 | 10.41 | 10.41 | 10.41 | 10.41 | 10.41 |
| 90 + 10 + 4 | 5.68 | 10.32 | 10.48 | | | 10.33 | 10.47 |
| 90 + 10 + 10 | 5.51 | 10.51 | 10.29 | | | 10.48 | 10.34 |
| 90 + 10 + 15 | 5.28 | 10.62 | 10.37 | | | 10.54 | 10.24 |
| 90 + 10 + 20 | 4.89 | 10.68 | 10.52 | 7.41 | 7.98 | 10.38 | 10.39 |

TABLE III

| | (100 ppm dosage) QM/BHT/Amine | | | | | | |
|---|---|---|---|---|---|---|---|
| Active Dosage, ppm | QM + BHT + TIPA | QM + BHT + TEA | QM + BHT + DEA | QM + BHT + QUADROL | QM + BHT + THEED | QM + BHT + MEA | QM + BHT + TBA |
| 90 + 10 + 0 | 7.8 | 7.8 | 7.8 | 7.8 | 7.8 | 7.8 | 7.8 |
| 90 + 10 + 4 | 4.65 | 7.62 | 7.69 | | | 7.66 | 7.74 |
| 90 + 10 + 10 | 4.27 | 7.55 | 7.6 | | | 7.54 | 7.61 |
| 90 + 10 + 15 | 3.88 | 7.67 | 7.49 | | | 7.61 | 7.52 |
| 90 + 10 + 20 | 3.52 | 7.68 | 7.57 | 5.54 | 5.83 | 7.53 | 7.63 |

TABLE IV

| | (200 ppm dosage) QM/2,6 DTBP/Amine | | | | | |
|---|---|---|---|---|---|---|
| Active Dosage, ppm | QM + 2,6DTBP + TIPA | QM + 2,6DTBP + QUADROL | QM + 2,6DTBP + THEED | QM + 2,6DTBP + TEA | QM + 2,6DTBP + DEA | QM + 2,6DTBP + MEA |
| 180 + 20 + 0 | 3.18 | 3.18 | 3.18 | 3.18 | 3.18 | 3.18 |
| 180 + 20 + 4 | 1.92 | 3.03 | 2.89 | 3.11 | 3.04 | 3.15 |
| 180 + 20 + 8 | 1.66 | 2.73 | 2.62 | 3.25 | 3.14 | 3.06 |
| 180 + 20 + 40 | 0.21 | 0.53 | 0.44 | 3.02 | 2.92 | 3.01 |

TABLE V

| | (200 ppm dosage) QM/BHA/Amine | | | | | |
|---|---|---|---|---|---|---|
| Active Dosage, ppm | QM + BHA + TIPA | QM + BHA + QUADROL | QM + BHA + THEED | QM + BHA + MEA | QM + BHA + DEA | QM + BHA + TEA |
| 180 + 20 + 0 | 6.96 | 6.96 | 6.96 | 6.92 | 6.92 | 6.92 |
| 180 + 20 + 4 | 2.89 | 4.46 | 4.29 | 6.87 | 6.94 | 6.77 |
| 180 + 20 + 8 | 2.4 | 3.91 | 3.68 | 6.65 | 6.7 | 6.73 |
| 180 + 20 + 40 | 0.34 | 1.69 | 1.54 | 6.51 | 6.57 | 6.63 |

TABLE VI (200 ppm dosage) QM/BHT/Amine

| Active Dosage, ppm | QM + BHT + TIPA | QM + BHT + QUADROL | QM + BHT + THEED | QM + BHT + MEA | QM + BHT + DEA | QM + BHT + TEA |
|---|---|---|---|---|---|---|
| 180 + 20 + 0 | 3.68 | 3.68 | 3.68 | 3.79 | 3.79 | 3.79 |
| 180 + 20 + 4 | 2.41 | 3.22 | 3.3 | 3.76 | 3.69 | 3.73 |
| 180 + 20 + 8 | 2.02 | 2.63 | 2.59 | 3.69 | 3.65 | 3.75 |
| 180 + 20 + 40 | 0.32 | 1.38 | 1.42 | 3.64 | 3.57 | 3.62 |

TABLE VII (200 ppm dosage) Individual compound

| Compound | Dosage, ppm (Active) | % Polymerization |
|---|---|---|
| TIPA | 200 | 16.16 |
| TEA | 200 | 16.9 |
| TBA | 200 | 16.21 |
| Quadrol | 200 | 14.64 |
| THEED | 200 | 14.34 |
| MEA | 200 | 15.47 |
| DEA | 200 | 15.27 |
| BHA | 200 | 17.14 |
| BHT | 200 | 15.68 |
| 2,6 DTBP | 200 | 16.31 |

TABLE VIII

| Time (min) | % Polymerization with 600 ppm of QM | % Polymerization with 600 ppm of QM and 85 ppm of 2,6 DTBP (100%) | % Polymerization with 600 ppm of QM and 85 ppm of HQ |
|---|---|---|---|
| 30 | 0 | 0 | 0 |
| 60 | 0.51 | 0.12 | 0.51 |
| 90 | 0.93 | 0.52 | 0.91 |
| 120 | 1.34 | 0.93 | 1.29 |
| 150 | 2.32 | 1.27 | 1.98 |
| 180 | 2.64 | 1.66 | 2.44 |
| 210 | 3.59 | 2.43 | 2.98 |
| 240 | 4.59 | 3.01 | 3.67 |
| 270 | 7.28 | 3.80 | 6.82 |
| 300 | 11.22 | 4.74 | 9.23 |

TABLE IX

| Time (min) | % Polymerization with 600 ppm of QM, 85 ppm of 2,6 DTBP (100%), and 18 ppm of TIPA | % Polymerization with 600 ppm of QM, 85 ppm of 2,6 DTBP (100%), and 30 ppm of TIPA |
|---|---|---|
| 30 | 0 | 0 |
| 60 | 0 | 0 |
| 90 | 0.15 | 0.14 |
| 120 | 0.24 | 0.20 |
| 150 | 0.29 | 0.22 |
| 180 | 0.41 | 0.30 |
| 210 | 0.54 | 0.38 |
| 240 | 0.90 | 0.68 |
| 270 | 1.41 | 0.87 |
| 300 | 2.22 | 1.15 |

TABLE X

| Time (min) | % Polymerization with 600 ppm of QM, 85 ppm of HQ, and 18 ppm of TIPA | % Polymerization with 600 ppm of QM, 85 ppm of HQ, and 30 ppm of TIPA |
|---|---|---|
| 30 | 0 | 0 |
| 60 | 0.40 | 0.35 |
| 90 | 0.90 | 0.72 |
| 120 | 1.07 | 0.93 |
| 150 | 1.91 | 1.48 |
| 180 | 2.18 | 1.96 |
| 210 | 2.61 | 2.21 |
| 240 | 3.52 | 3.03 |
| 270 | 6.62 | 5.79 |
| 300 | 9.05 | 7.52 |

As can be observed from above experiments, on addition of 18 ppm of TIPA in 685 ppm of combination of "QM (600 ppm) and 2-6 DTBP (85 ppm)", the "% polymerization" reduces substantially.

Similarly, on addition of 30 ppm of TIPA in 685 ppm of combination of "QM (600 ppm) and 2-6 DTBP (85 ppm)", the "% polymerization" reduces substantially.

As can be observed from above experiments, on addition of 18 ppm of TIPA in 685 ppm of combination of "QM (600 ppm) and HQ (85 ppm)", the "% polymerization" does not reduce substantially.

Similarly, on addition of 30 ppm of TIPA in 685 ppm of combination of "QM (600 ppm) and HQ (85 ppm)", the "% polymerization" does not reduce substantially.

All of above experiments confirm that only the present additive compositions comprising mixture of QM and phenolic compound and aliphatic tertiary amine of the present invention result in improvement of polymerization inhibition efficiency of the prior art additive consisting of a combination of QM and phenolic compound.

The above findings confirm that the present composition is more economical and environment friendly than prior art composition consisting of mixture of QM and phenolic compounds.

The above findings also confirm synergistic, surprising and unexpected effects of the present composition.

Above experimental results also confirm that the presently provided composition is far superior than the prior art additive compositions, and hence, has technical advantages and surprising effects over the prior art additives.

The invention claimed is:

1. An improved amine based additive composition for controlling and inhibiting polymerization of aromatic vinyl monomers including styrene comprising:
   (A) one or more quinone methide or derivatives thereof (QM),
   (B) one or more phenolic compounds, and
   characterized in that the said composition further comprises:
   (C) at least one amine comprising aliphatic tertiary amine containing —OH group in the alkyl chain;

wherein the quinone methide or derivatives thereof (QM) comprises benzyl quinone methide;

wherein the phenolic compound comprises 2,6-di-tert-butyl phenol (2,6 DTBP), butylated hydroxy anisole (BHA), butylated hydroxy toluene (BHT), or a mixture thereof; and wherein the aliphatic tertiary amine comprises tri-isopropanol amine or tris(2-hydroxypropyl)amine (TIPA), N,N,N',N'-Tetrakis (2-hydroxyethyl) ethylene-diamine (THEED), N,N,N',N'-Tetrakis (2-hydroxypropyl) ethylene-diamine, or mixture thereof.

2. The improved amine base additive composition as claimed in claim 1, wherein the quinone methide or derivatives thereof (QM) comprises 4-benzylidene, 2,6-di-tert-butyl cyclohexa-2,5-dienone.

3. A method of using the additive composition as claimed in claim 1 to control and inhibit polymerization of aromatic vinyl monomers including styrene, wherein the method comprises treating the aromatic vinyl monomers including styrene with the said additive composition.

4. The method as claimed in claim 3, wherein the additive composition is added to the stream containing aromatic vinyl monomers including styrene in an amount varying from 0.01 ppm to 5000 ppm by weight of the stream of the monomers including styrene.

5. The method as claimed in claim 3, wherein the additive composition is used at a temperature varying from 50 degree C. to 180 degree C.

6. The method as claimed in claim 3, wherein the additive composition is added to the stream containing aromatic vinyl monomers including styrene in an amount varying from 0.1 ppm to 3000 ppm by weight of the stream of the monomers including styrene.

7. The method as claimed in claim 3, wherein the additive composition is added to the stream containing aromatic vinyl monomers including styrene in an amount varying from 1 ppm to 2000 ppm by weight of the stream of the monomers including styrene.

8. The method as claimed in claim 3, wherein the additive composition is added to the stream containing aromatic vinyl monomers including styrene in an amount varying from 5 ppm to 2000 ppm by weight of the stream of the monomers including styrene.

9. The method as claimed in claim 3, wherein the additive composition is used at a temperature varying from 60 degree C. to 180 degree C.

10. A method for controlling and inhibiting polymerization of aromatic vinyl monomers including styrene, wherein the method comprises adding the said additive composition as claimed in claim 1 to the stream comprising aromatic vinyl monomers including styrene.

11. The method as claimed in claim 10, wherein the additive composition is added to the stream containing aromatic vinyl monomers including styrene in an amount varying from 0.01 ppm to 5000 ppm by weight of the stream of the monomers including styrene.

12. The method as claimed in claim 10, wherein the additive composition is used at a temperature varying from 50 degree C. to 180 degree C.

13. The method as claimed in claim 10, wherein the additive composition is added to the stream containing aromatic vinyl monomers including styrene in an amount varying from 0.1 ppm to 3000 ppm by weight of the stream of the monomers including styrene.

14. The method as claimed in claim 10, wherein the additive composition is added to the stream containing aromatic vinyl monomers including styrene in an amount varying from 1 ppm to 2000 ppm by weight of the stream of the monomers including styrene.

15. The method as claimed in claim 10, wherein the additive composition is added to the stream containing aromatic vinyl monomers including styrene in an amount varying from 5 ppm to 2000 ppm by weight of the stream of the monomers including styrene.

16. The method as claimed in claim 10, wherein the additive composition is used at a temperature varying from 60 degree C. to 180 degree C.

17. A method of using the additive composition as claimed in claim 2 to control and inhibit polymerization of aromatic vinyl monomers including styrene, wherein the method comprises treating the aromatic vinyl monomers including styrene with the said additive composition.

18. A method for controlling and inhibiting polymerization of aromatic vinyl monomers including styrene, wherein the method comprises adding the said additive composition as claimed in claim 2 to the stream comprising aromatic vinyl monomers including styrene.

* * * * *